(12) United States Patent
Neal et al.

(10) Patent No.: US 7,339,754 B2
(45) Date of Patent: Mar. 4, 2008

(54) SWITCHING ILLUMINATING TWEEZERS WITH MAGNIFIER

(76) Inventors: Phillip H. Neal, 171 Terrace Ave., San Rafael, CA (US) 94901; Michael J. Liebowitz, 1229 Plumleigh La., Concord, CA (US) 94521; Margaret S. Neal, 171 Terrace Ave., San Rafael, CA (US) 94901

( * ) Notice: Subject to any disclaimer, the term of this patent is extended or adjusted under 35 U.S.C. 154(b) by 0 days.

(21) Appl. No.: 11/308,858

(22) Filed: May 16, 2006

(65) Prior Publication Data
US 2007/0024997 A1 Feb. 1, 2007

Related U.S. Application Data

(60) Provisional application No. 60/594,940, filed on May 20, 2005.

(51) Int. Cl.
*G02B 27/02* (2006.01)
(52) U.S. Cl. .................. 359/802; 359/803; 294/99.2
(58) Field of Classification Search ............... 359/802, 359/803, 798; 294/99.2; 606/211
See application file for complete search history.

(56) References Cited

U.S. PATENT DOCUMENTS 4,524,647 A * 6/1985 Holoff et al. .............. 294/99.2
6,951,403 B2 * 10/2005 Bennett, Jr. .................. 362/98
7,178,847 B1 * 2/2007 Mui .......................... 294/99.2

FOREIGN PATENT DOCUMENTS

DE 102 490 A1 * 11/2004

* cited by examiner

Primary Examiner—Timothy Thompson
(74) Attorney, Agent, or Firm—Michael E. Woods

(57) ABSTRACT

An apparatus and method for improving local illumination by a personal care implement, such as tweezers, tongs, pinchers and the like. The apparatus includes a first arm terminating at one end in a first gripping edge; a second arm, coupled to and biased away from said first arm, terminating at one end in a second gripping edge springingly engaging with said first gripping edge; an illumination system directing illumination into a field-of-view in an "ON" mode and said illumination system including an "OFF" mode in which said illumination system is inactive; a magnification system including a lens having a focus; and an illumination boom, coupled to said arms, for positioning said lens and a light source of said illumination system between a stowed position and an operating position, said stowed position engaging said OFF mode and said operating position including a stop to configure said boom and engage said ON mode to include said gripping edges within said field-of-view and at said focus.

7 Claims, 2 Drawing Sheets

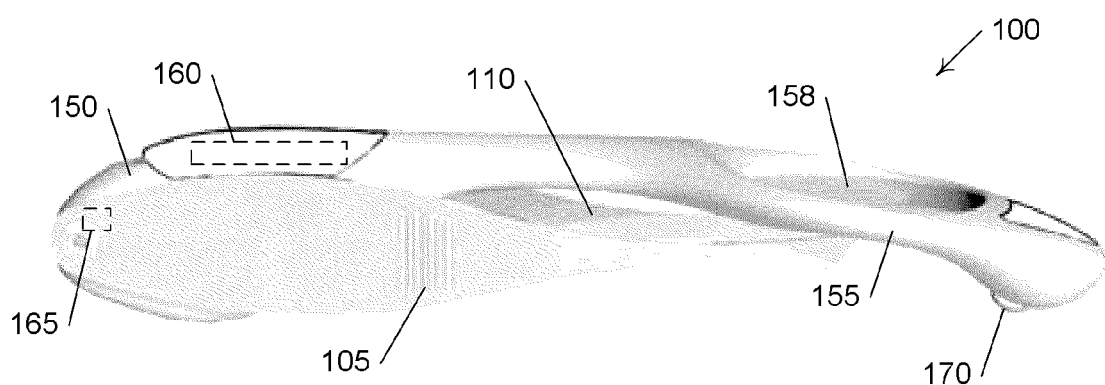
FIGURE_1
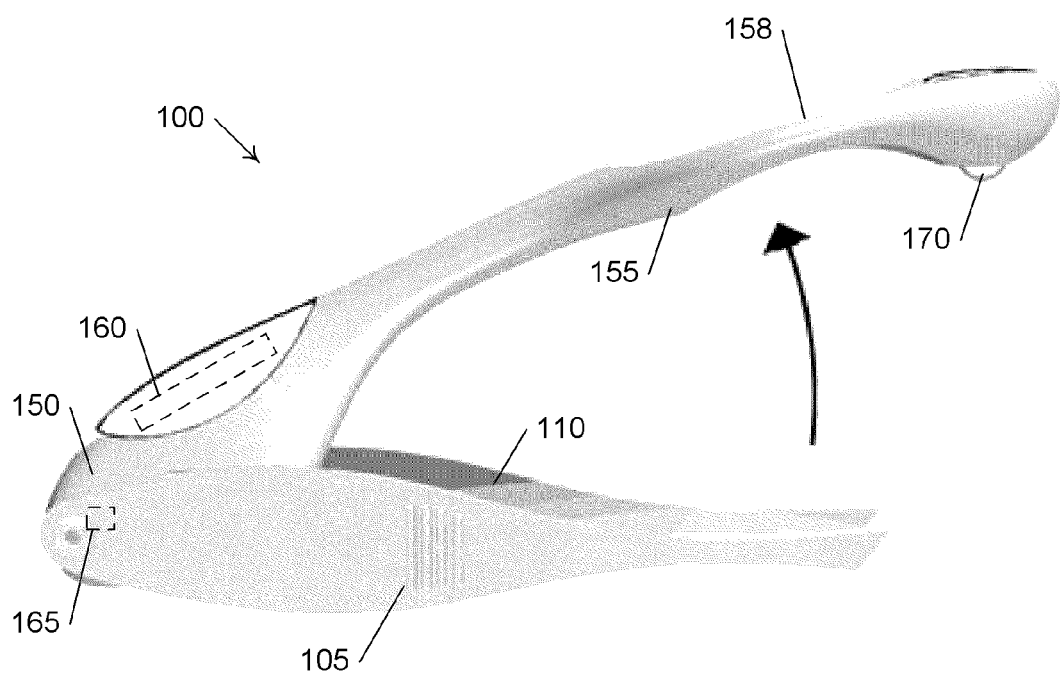
FIGURE_2

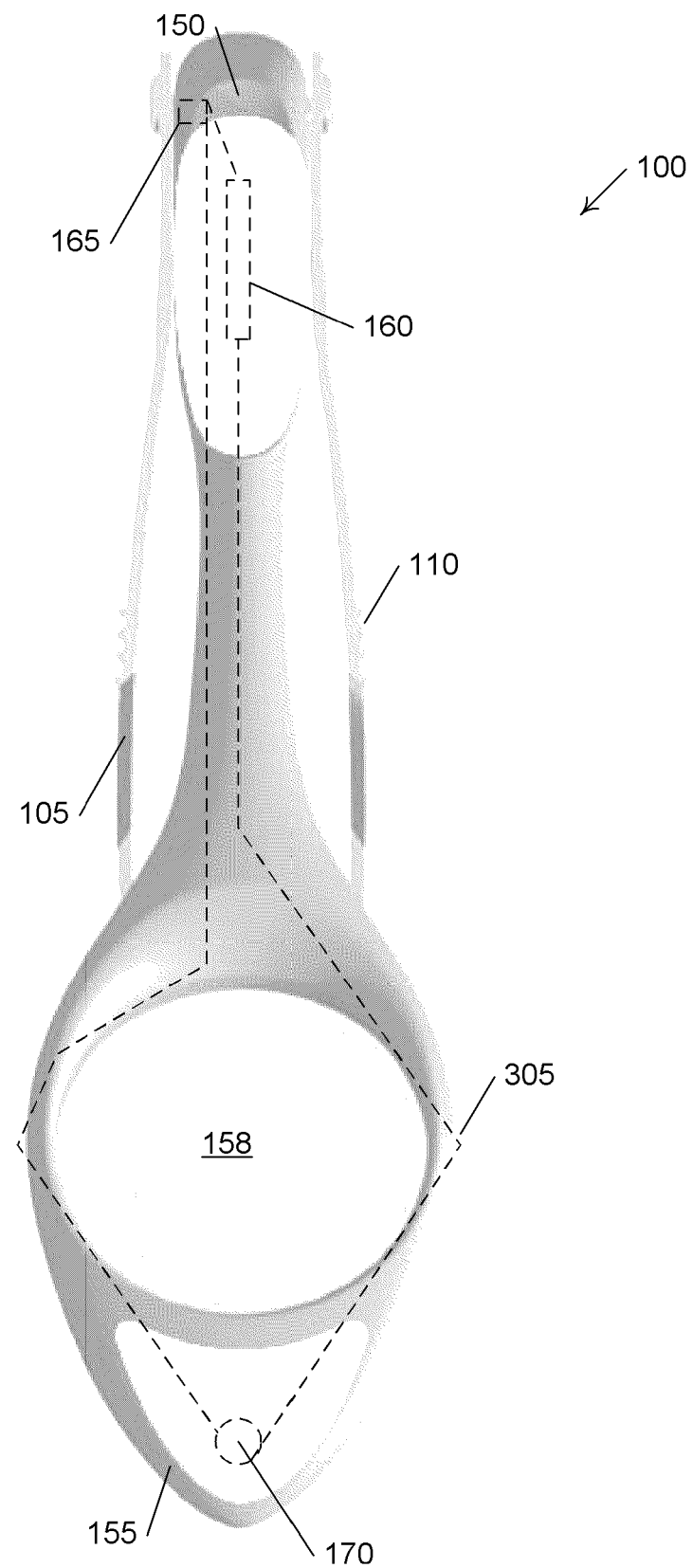
FIGURE_3

SWITCHING ILLUMINATING TWEEZERS WITH MAGNIFIER

CROSS REFERENCE TO RELATED APPLICATIONS

The present application is related to and claims benefit of U.S. Application 60/594,940 entitled "Switching Illuminating Tweezers With Magnifier" filed 20 May 2005, and is related to U.S. application Ser. No. 11/308,857 entitled "Switching Illuminating Nail Clippers," filed concurrently that claims benefit of related U.S. Application No. 60/594,937 entitled "Switching Illuminating Nail Clippers," filed 20 May 2005, and is related to U.S. application Ser. No. 11/308,859 entitled "Switching Illuminating Scissors," filed concurrently that claims benefit of related U.S. Application No. 60/594,938 entitled "Switching Illuminating Scissors," filed 20 May 2005, and is related to U.S. application Ser. No. 11/308,860 entitled "Packaging Arrangement Having Package Feature For Biasing A Switch From An On Mode To An Off Mode," filed concurrently that claims benefit of related U.S. Application No. 60/594,939 entitled "Packaging Arrangement Having Package Feature For Biasing A Switch From An On Mode To An Off Mode," filed 20 May 2005 and each related application incorporated by reference in their entireties for all purposes.

BACKGROUND OF THE INVENTION

The present invention relates generally to personal care products, and more specifically to illuminating implements for use by a caregiver when providing personal care to its charge.

Personal care products and tools have evolved and been developed for attending to personal hygiene of a human body. The evolution and development of these products and tools has largely been to enhance products for use by an individual in performance of their own personal care. When only a single person is involved, and that person controls the timing, urgency, and manner of performance of the product or tool, different parameters of the product or tool are optimized, created, emphasized and/or implemented.

However, when providing personal care for another person, particularly to a very young child or senior adult, the caregiver does not always control the timing, urgency, and manner of performance. Specifically, the caregiver may desire to provide various personal care procedures at times or locations that are not otherwise optimal. One common environmental factor that may not be able to be optimized in such situations is a level of ambient light in the vicinity of the procedure.

Besides these concerns, when providing personal care for another person, particularly to a very young child or senior adult, many caregivers prefer to enhance the level of care provided, including greater attention to safety procedures and use of safer tools. This is true even in situations where the caregiver may control some of the timing, urgency, and manner of performance, such as to increase a general level of ambient light. For this example, the caregiver may desire to precisely increase a level of illumination for use of personal care tool when a very young child or senior adult is involved.

Beyond these concerns, factors for acceptability and adoption of personal care procedures include ease of use, convenience, efficiency, and effectiveness. Portable illumination components (e.g., flashlights) have existed separate and distinct from tools so conventional systems either require coordination of the light source and a tool, or various forms of integration have been developed to mate a light to a tool. Some of the integration are simple physical connections that keep the tool and the light source together while others actually try to achieve a more synergistic combination. Maintaining ease of use, convenience, efficiency, and effectiveness becomes more challenging as multiple diverse functions are merged together. In the example of personal care applied to a young child or senior adult, enabling single-handed use and operation while providing the multiple diverse functions becomes increasingly difficult yet even more challenging. A caregiver often must use one hand for the tool and the other to interact with the young child or senior adult.

It should not be missed that improvements to procedures and tools that aid a care giver when attending to young children and senior adults may in many cases also assist in self-administration and self-care. Thus, it is a consideration that improvements to procedures and tools for administration to others not degrade or adversely affect self-administration.

One consequence of these factors is that some personal care products and tools are sometimes equipped with lights. Such conventional personal care products and tools have ON-OFF switches to control the light source independent from operation. The light for these devices is thus not always active and useful when the user operates the device. In some cases, operation of the device is delayed or interrupted while the light is manually illuminated. In other cases, the light is left on beyond the time of use because the switch was not manually returned to the off position, decreasing the longtime usefulness of the product or tool. Caregivers would prefer to have a product or tool that does not delay or interrupt their use, and one that does not have a premature end to its anticipated usefulness.

Today's consumer is inundated with offers to sell many different products and services, some of which may actually be of interest to the potential consumer. In some instances, interactive packaging (also sometimes referred to as "Try Me" packaging) may enhance an appeal of a product. For such products, it is advantageous to provide appropriate "Try Me" packaging. However, the state of the art does not permit a priori knowledge as to which products would be benefited from being packaged in an interactive format. Developing a superior product does not always equate with increased sales, at least until the market knows and understands the new product. There are many consumer products that incorporate microprocessors and microcontrollers that may include "Try Me" routines or programs that effectively address some of the concerns of "Try Me" packaging. However, for articles of manufacture that do not include electronic controllers, designing a product and its packaging to implement "Try Me" retailing is more challenging. Some conventional products have developed use of momentary switches or special multi-function switches so that a "continuous on" mode of the switch may be disabled by the packaging while providing access to an "On while pressed" mode of the switch.

What is needed are personal care products, tools, and procedures that address and overcome the deficiencies of the current products and tools; specifically what is needed are products, tools, and procedures for simply and efficiently increasing a level of illumination at the operational point of personal care products, tools, and procedures. Additionally, designing such products, tools, and procedures so that they include features or functions that may be emphasized in suitable interactive packaging is also beneficial.

BRIEF SUMMARY OF THE INVENTION

Disclosed is an apparatus and method for improving local illumination by a personal care implement, such as tweezers, tongs, pinchers and the like. The apparatus includes a first arm terminating at one end in a first gripping edge; a second arm, coupled to and biased away from said first arm, terminating at one end in a second gripping edge springingly engaging with said first gripping edge; an illumination system directing illumination into a field-of-view in an "ON" mode and said illumination system including an "OFF" mode in which said illumination system is inactive; a magnification system including a lens having a focus; and an illumination boom, coupled to said arms, for positioning said lens and a light source of said illumination system between a stowed position and an operating position, said stowed position engaging said OFF mode and said operating position including a stop to configure said boom and engage said ON mode to include said gripping edges within said field-of-view and at said focus.

Preferred embodiments of the present invention include personal care products, tools, and procedures that address and overcome the deficiencies of the current products and tools; specifically products, tools, and procedures that simply and efficiently increase a level of illumination at the operational point of personal care products, tools, and procedures. Additionally, the preferred embodiments include features or functions that may be emphasized in suitable interactive packaging.

BRIEF DESCRIPTION OF THE DRAWINGS

FIG. 1 is a lateral view of a preferred embodiment of the present invention for an illuminating tweezers in a closed configuration;

FIG. 2 is a lateral view of the illuminating tweezers of FIG. 1 in an open mode with an illumination boom in an operational mode; and FIG. 3 is a top view of the illuminating tweezers shown in FIG. 2.

DETAILED DESCRIPTION OF THE INVENTION

The present invention provides an apparatus and method for an illuminating tweezing implement as well as implementation of a design paradigm for enabling "Try Me" retail packaging with a function controlled by physical manipulation of a handle or lever included as part of the product. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

FIG. 1 is a lateral view of a preferred embodiment of the present invention for an illuminating tweezers 100 in a closed configuration. Tweezers 100 includes a first plate 105 and a second plate 110 coupled together at one fixed end and having pincers appropriate for the specific application/implementation deployed at another end of the plates. The plates thus include cooperating pincher edges, with plate 105 and plate 110 conventionally interconnected to produce a tweezing implement. This implement, as shown, is configured for generic tweezing, such as for removal of splinters or other small objects but as well-known, other configurations for the plates and pinchers may be adapted to grasp and hold other objects.

Tweezers 100 include, in addition to the components of the tweezing implement, an illumination subsystem that includes a housing 150 supporting an illumination boom 155 and a magnifier 158, housing 150 moveably (e.g., rotationally) coupled to the fixed ends of plate 105 and plate 110. Housing 150 contains a battery 160 and a switch 165 for controlling an illumination source 170 (such as a white LED) and is positioned between a back end of plate 105 and plate 110. In the closed configuration shown in FIG. 1, tweezers 100 has illumination boom 155 folded against plate 105 and plate 110 in a stowed position.

FIG. 2 is a lateral view of the illuminating tweezers of FIG. 1 in an open mode with illumination boom 155 rotated into an operational position. In the open mode, tweezers 100 operate in conventional fashion in which a user may springingly engage and disengage cooperating pinching edges disposed on ends of plate 105 and plate 110. External lateral portions of the plates provide for grips so that the pinching edges are easily manipulated by squeezing and relaxing the plates relative to each other. In the preferred embodiments, the grips are adapted to enhance the tweezing experience, which may include widening, lengthening, conforming, and other modifications to the grip dimensions, as well as material selection (e.g., cushioning) to enhance operation of the tweezing subsystem.

Engaging the operational mode of illumination boom 155 exposes illumination source 170 and positions source 170 at a position between a user and the pinching edges to illuminate a field-of-view that includes the pinching edges, some appropriate radius around the pinching edges, and within a field-of-view of magnifier 158. In the preferred embodiment, source 170 is powered by battery 160 and an ON/OFF status of source 170 is controlled by switch 165. Switch 165 is coupled to illumination boom 155 so movement of boom 155 between the operational mode and the stowed mode controls switch operation.

As shown in this preferred embodiment, boom 155 rotates to the operational position when moving between the stowed and the operation modes and switch 165 is coupled to a pivot point so the rotation controls operation of switch 165. In the most preferred embodiment, as explained below, the configuration of switch 165 in relation to ON/OFF switching responsive to rotation is established so that source 170 is off except for the last few degrees (e.g., about five degrees) of rotation, though implementations and embodiments may vary.

A threshold for determining the ON/OFF responsiveness of switch 165 varies in different embodiments and implementations, however the preferred embodiment more easily permits use of a package-enhancing features during marketing, such as a "Try Me" package. Thus the features of incorporating switch 165 into tweezers 100 in a manner that source 170 is responsive to operational deployment and establishing thresholds for ON/OFF responsiveness so that a desired feature (in this case illumination) is enabled during a small end-portion of boom-deploying rotation, combines to produce in this implementation characteristics for tweezers 100 that enable consumer-level retail "Try Me" packaging. (Such as, for example, providing packaging that lightly biases illumination boom 155 into a rotational position close to the threshold, but with source 170 inactive.) The packaging, in permitting a prospective customer to move boom 155 past the threshold to activate source 170 interactively presents the illumination feature, but returns source 170 to the inactive status when the prospective customer is done interacting with the packaging. Providing the boom close to the threshold, near the extreme end of range of movement, and using a lever arm, permits the biasing mechanism in the packaging to be implemented efficiently and inexpensively. For example, foam may be adhered to appropriate portions of a package in contact with the actuating handle. Other biasing systems, e.g., metal springs and the like, may also be used. This configuration permits light force, short distance biasing systems to be used that are often quite simple, effective, virtually error-free, and inexpensive.

FIG. 3 is a top view of illuminating tweezers 100 shown in FIG. 2. FIG. 3 illustrates (functionally—not the actual path) an electrically conductive path 305 that forms an electrical circuit for battery 160, switch 165 and source 170. Current in this electrical circuit is controlled by switch 165, and switch 165 is controlled in turn by a positional rotation of illumination boom 155.

In operation, a user opens tweezers 100 by rotating boom 155 to permit tweezing operations. Rotating boom 155 from the stowed position to the operational position provides illumination from source 170 to flood the pinching edges and an appropriate distance therearound, with magnifier 158 disposed in housing 150 near source 170 so that the illuminated pinching edges are within focus. Switch 165, sometime during this rotation of boom 155 as determined by design considerations specific to an embodiment and implementation, closes conductive path 305 to cause battery 160 to produce an electrical potential across source 170 so that source 170 illuminates the tweezing zone. When tweezing is complete, or illumination is no longer needed or desired in the tweezing zone, the user rotates boom 155 from the operational mode to the stowed mode, opening path 305 and extinguishing source 170. When boom 155 is in the stowed mode, boom 155 and the plates protect source 170 and help to keep it clean and undamaged.

Other variations and modifications are possible without departing from the spirit and scope of the present invention, some of these variations and modifications are described above, Other variations and modifications include changes to battery location and a location/operation of boom 155. Boom 155 variations may include differences in stowage/ operational locations (e.g., illuminating from a location near a rear of the housing and the like), as well as a manner of transitioning between these modes besides or in addition to rotating (e.g., sliding, shifting, expanding, traversing, and the like). Further modifications include placement of the illumination source and the magnifier on the boom. Different configurations may provided different orientations and configurations and arrangements of these components, including a placement and ordering on the boom. Additional modifications include triggering the illumination subsystem based upon squeezing/releasing the plates. Different switches and triggering systems may be employed to provide for the illumination subsystem to be responsive to operational motion of the tweezers.

In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures may also be implemented in a more separated or integrated manner, or even removed or rendered as inoperable in certain cases, as is useful in accordance with a particular application. It is also within the spirit and scope of the present invention to implement a program or code that may be stored in a machine-readable medium or transmitted using a carrier wave to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims.

The above-described arrangements of apparatus and methods are merely illustrative of applications of the principles of this invention and many other embodiments and modifications may be made without departing from the spirit and scope of the invention as defined in the claims.

These and other novel aspects of the present invention will be apparent to those of ordinary skill in the art upon review of the drawings and the remaining portions of the specification. Therefore, the scope of the invention is to be determined solely by the appended claims.

What is claimed as new and desired to be protected by Letters Patent of the United States is:

1. An apparatus, comprising:
    a first arm terminating at one end in a first gripping edge;
    a second arm, coupled to and biased away from said first arm, terminating at one end in a second gripping edge springingly engaging with said first gripping edge;
    an illumination system directing illumination into a field-of-view in an "ON" mode and said illumination system including an "OFF" mode in which said illumination system is inactive;
    a magnification system including a lens having a focus; and
    an illumination boom, coupled to said arms, for positioning said lens and a light source of said illumination system between a stowed position and an operating position, said stowed position engaging said OFF mode and said operating position including a stop to configure said boom and engage said ON mode to include said gripping edges within said field-of-view and at said focus
    wherein said illumination boom is pivotally coupled between said arms, wherein said stowed position positions said boom between said arms, and wherein said operating position includes rotating said boom from between said arms to include said gripping edges within said field of view at said focus from above said gripping edges.

2. The apparatus of claim 1 wherein said illumination system includes a switchable, battery-operated light emitting diode (LED).

3. The apparatus of claim 1 wherein said illumination system includes a switch in series with a battery-operated light emitting diode (LED), and wherein said illumination boom controls said switch with said LED illuminated when said boom is in said operating position and said LED inactive when said boom is in said stowed position.

4. A method, the method comprising:
    a) providing a tweezers having a pair of opposing arms each including a mating gripping edge with a moveable illumination subsystem integrated into a handle wherein said illumination subsystem is responsive to a switch coupled to a handle wherein said handle includes an illumination boom supporting a light source and wherein said illuminating boom is pivotally coupled between said arms, wherein said illuminating subsystem includes a stowed position that positions said boom between said arms and further includes an operating position;
    b) actuating said moveable illumination subsystem by positioning said handle into said operating mode from said stowed position that directs illumination from said illumination subsystem into a field-of-view that includes a pinching edge of said tweezers wherein said handle is positioned outside of a plane containing both arms of said tweezers.

5. A method, comprising:
    a) rotating a light source, coupled to an illuminating boom rotatably disposed between a pair of opposing mating arms of a tweezers with each said mating arm including a pinching edge, from a stowed mode having said illumination boom disposed outside a plane containing said arms; and
    b) actuating said light source responsive to said rotation of said illuminating boom outside of said plane.

6. The method of claim 5 wherein said illumination boom includes a magnifier including a focal point approximately at said pinching edge when said light source is active.

7. The method of claim 5 wherein said light source is activated within about five degrees of an end of a range of rotation for said illumination boom.

* * * * *